US008354637B2

(12) United States Patent
Tanaka

(10) Patent No.: US 8,354,637 B2
(45) Date of Patent: Jan. 15, 2013

(54) METHOD FOR OBTAINING CRYSTAL LATTICE MOIRE PATTERN AND SCANNING MICROSCOPE

(75) Inventor: Hiroki Tanaka, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 69 days.

(21) Appl. No.: 12/890,064

(22) Filed: Sep. 24, 2010

(65) Prior Publication Data

US 2011/0073757 A1 Mar. 31, 2011

(30) Foreign Application Priority Data

Sep. 25, 2009 (JP) ................................. 2009-221317

(51) Int. Cl.
*G01N 23/04* (2006.01)
*G01N 23/00* (2006.01)

(52) U.S. Cl. ....................................... 250/307; 250/306

(58) Field of Classification Search .................. 250/307, 250/311, 306
See application file for complete search history.

(56) References Cited

U.S. PATENT DOCUMENTS

| | | | | |
|---|---|---|---|---|
| 4,567,369 A | * | 1/1986 | Smith et al. .................... | 250/397 |
| 6,606,149 B1 | * | 8/2003 | Ogasawara et al. ............ | 356/121 |
| 7,476,882 B2 | * | 1/2009 | Nakayama et al. ........ | 250/492.3 |
| 7,633,064 B2 | * | 12/2009 | Tsuneta et al. ................ | 250/310 |
| 2005/0045819 A1 | * | 3/2005 | Bedell et al. ................... | 250/307 |
| 2006/0255272 A1 | * | 11/2006 | Nakayama et al. ............ | 250/310 |
| 2007/0229835 A1 | * | 10/2007 | Smolyaninov et al. ....... | 356/445 |
| 2009/0224169 A1 | * | 9/2009 | Sawada ...................... | 250/396 R |
| 2010/0252735 A1 | * | 10/2010 | Hytch et al. ................... | 250/311 |

FOREIGN PATENT DOCUMENTS

JP 2007-315877 12/2007

OTHER PUBLICATIONS

Su, et al., "Scanning Moire Fringe Imaging by Scanning Transmission Electron Microscopy", Ultramicroscopy, Feb. 2010; 110(3):229-33, Epub Nov. 26, 2009.*
Guo, et. al.; Nanometre moire fringes in scanning tunneling microscopy of surface lattices, Nanotechnology 15 (2004) 991-995.*
Su, et al., "Scanning Moire Fringe Imaging by Scanning Transmission Electron Microscopy", Ultramicroscopy, Feb. 2010; 110(3):229-33, Epub Nov. 26, 2009, 2 pages.

* cited by examiner

*Primary Examiner* — David A Vanore
*Assistant Examiner* — Wyatt Stoffa
(74) *Attorney, Agent, or Firm* — Oblon, Spivak, McClelland, Maier & Neustadt, L.L.P.

(57) ABSTRACT

A method for taking a crystal lattice moiré pattern of a crystal structure using a scanning microscope, and the scanning microscope implementing the method, arranges multiple virtual lattice points periodically corresponding to the crystal structure and an orientation thereof, on a scan plane of the crystal structure, detects signals from the multiple virtual lattice points, generated by an incident probe of the scanning microscope, and generates data of the crystal lattice moiré pattern, based on the detected signals.

12 Claims, 14 Drawing Sheets

Fig. 5A
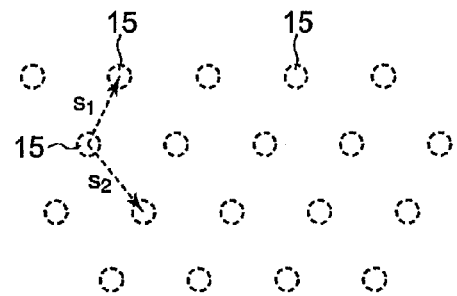
Fig. 5B            Fig. 5C
FIG. 6
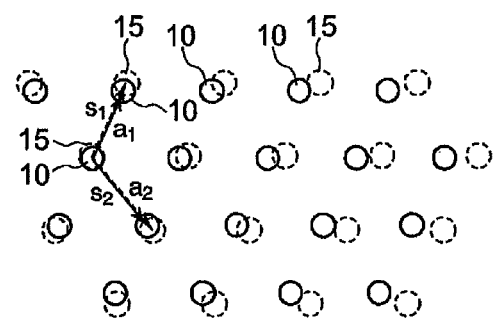

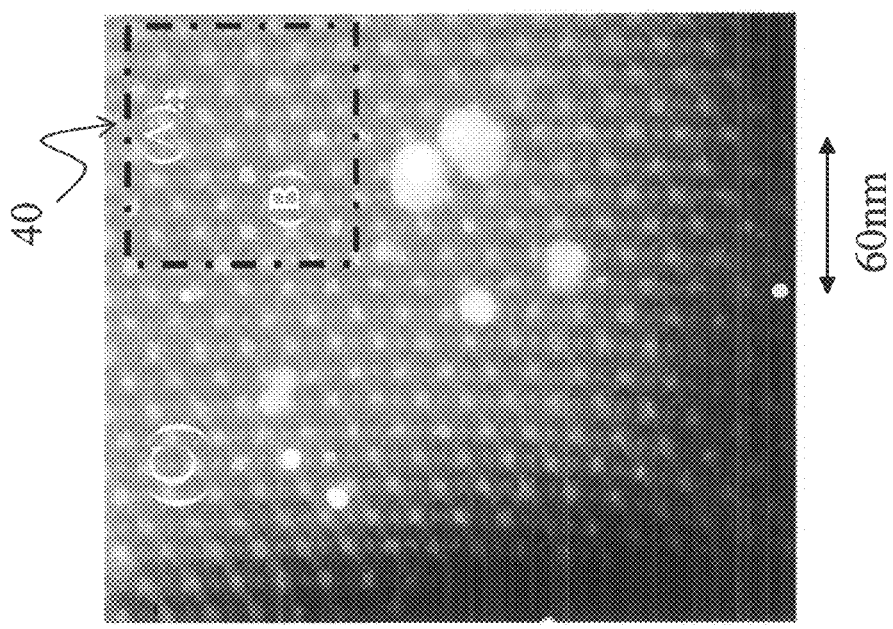

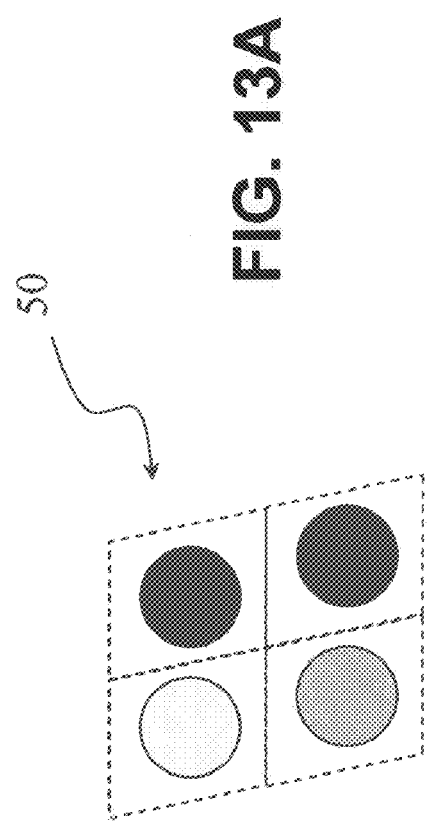
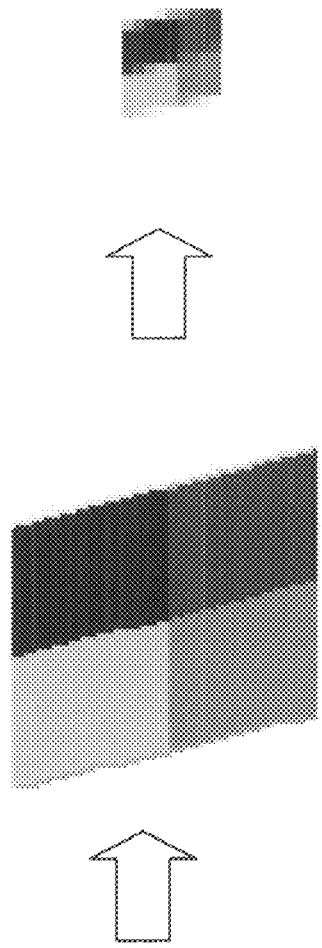
FIG. 13A
FIG. 13B
FIG. 13C

METHOD FOR OBTAINING CRYSTAL LATTICE MOIRE PATTERN AND SCANNING MICROSCOPE

CROSS-REFERENCE TO RELATED APPLICATIONS

This application is based upon and claims the benefit of priority from Japanese Patent Application No. 2009-221317, filed Sep. 25, 2009, the entire contents of which are incorporated herein by reference.

FIELD

Embodiments described herein relate generally to a method for obtaining a crystal lattice moiré pattern and a scanning microscope.

BACKGROUND

A Transmission Electron Microscope, hereinafter TEM, and a Scanning Transmission Electron Microscope, hereinafter STEM, have enhanced high spatial resolution at an atomic level, so that a crystal lattice image can be observed. A crystal lattice has a periodic structure inside thereof, and there are several useful measuring methods using this periodicity.

Especially, the STEM can observe atomic columns directly by a high angle annular dark field, hereinafter HAADF. The STEM has a merit of being able to observe multiple signals including this HAADF signal all at once. However, STEM images take longer time to acquire a single image than TEM images because it uses a scanning method. For instance, it takes 1 minute or more for obtaining enough signal intensity to observe a crystal lattice image of 50 nm square area in a typical STEM measurement. A commercially-supplied STEM has positional instability of about 1 nm per minute. Atomic distances of most materials are less than 1 nm. If the required accuracy is less than one atomic lattice distance with the image whole, the accuracy cannot be fulfilled.

Further, it is incompatible in present conditions to keep a high spatial resolution able to observe the crystal lattice image, and to obtain an image of a large area. Under the condition of high spatial resolution for scan steps, a scanning time is proportional to the scanning area. For instance, if the scale (magnification) of the scanning region is changed by 10 times, the scanning area and time become huge with changing by 100 times, because an area is proportional to the $2^{nd}$ power. Thus, a high spatial resolution in a large area takes time, which causes a large shift of the image, and high accuracy observation becomes difficult.

BRIEF DESCRIPTION OF THE DRAWINGS

In the figures:
FIGS. 5A to 5C explain virtual lattice points and scan;
FIG. 6 explains crystal lattice points and virtual lattice points;
FIGS. 10A to 10C explain moiré patterns in a perfect crystal area and a strain area;
FIGS. 13A to 13C explain processing of detected signals from virtual lattice points.

DETAILED DESCRIPTION

Figure 1:
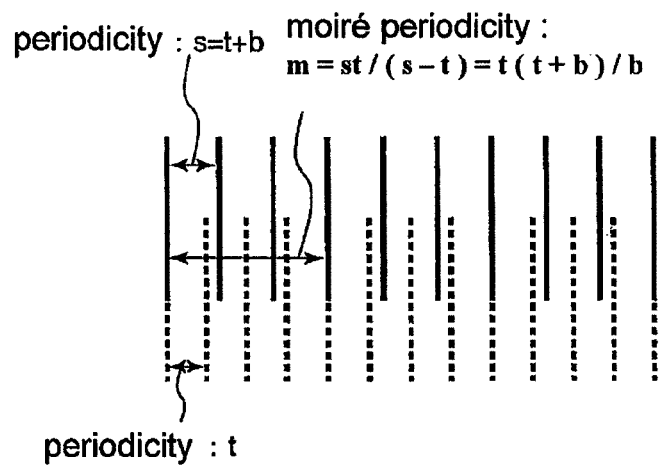
FIG. 1 explains a moiré periodicity.

Before explaining the embodiments, an outline is explained.

According to a first aspect of the present disclosure, a method for taking a crystal lattice moiré pattern of a crystal structure using a scanning microscope includes:
arranging multiple virtual lattice points periodically corresponding to the crystal structure and an orientation thereof, on a scan plane of the crystal structure;
detecting signals from the multiple virtual lattice points, generated by an incident probe; and
generating the crystal lattice moiré pattern of the crystal structure, based on the detected signals.

According to a second aspect of the present disclosure, a scanning microscope includes:
a beam generator generating a beam made of charged-particles;
a deflection section deflecting the beam;
an objective lens making the beam concentrate on a scan plane of a crystal structure;
a detector detecting signals generated from the crystal structure and the beam;
a calculation/setting unit calculating and setting positions of multiple virtual lattice points being in alignment periodically corresponding to the crystal structure and an orientation thereof on a scan plane of the crystal structure;
a beam controller sending control signals to the deflection section and making the beam emit at the positions of the multiple virtual lattice points; and
a moiré pattern generator generating a crystal lattice moiré pattern of the crystal structure, based on the detected signals.

Embodiments are made in consideration of the above-mentioned situation, and some embodiments of this invention may provide a method for taking a crystal lattice moiré pattern and a scanning microscope which can obtain the moiré pattern of the crystal lattice image, with high accuracy and in a short time.

A moiré interference pattern is a phenomena in which a new periodic pattern is generated from a superposition of two or more periodic patterns. Thereby, a slight change from a perfect periodicity is detectable by measuring a large scale of the moiré interference patterns. Here, a typical measured object, a cross-sectional image of a natural crystal, is surely a two-dimensional periodic lattice. The applicants recognized if an STEM can observe the moiré interference patterns in two dimensions made by a beam scan on the measured object, it can observe a large area of the measured object in a short time. Namely, the positioning instability problem of the STEM can be overcome by a short time observation of the moiré interface patterns.

Embodiments describe how to obtain and analyze the two-dimensional moiré pattern of various two-dimensional crystal lattice images formed on a natural crystal section.

In this embodiment, the two-dimensional moiré pattern is produced by setting two-dimensional virtual lattice points and obtaining signals from the points. Consequently, scanning microscopy and moiré fringe regarding the principle are explained before the embodiment.

<Scanning Microscopy Technique>

In a scanning microscopy technique, first, an incident probe as a particle including a charged particle such as an electron and an ion, an elemental particle and among other things, irradiates or interacts on a measured object. Second, a transmission, a reflection, and a scattering of the incident probe from the measured object, or secondary electrons or light caused by the interaction with the incident probe and the measured object, are detected in synchronization with each scanning point. Third, the image is obtained by plotting the detected signals.

<Scanning Area and Time>

In the case of a high resolution image such as a crystal lattice image being close to a resolution limit, a scanning step is set to be smaller than the resolution. For instance, when the resolution is 0.1 nm, the scanning step is 0.02 nm, and the image has 1000×1000 pixels, a field of view becomes a very small area, 20 nm×20 nm. To obtain a large image area, a lot of pixels and an immense amount of measuring time proportional to the pixels are required. And such a long measuring time causes a huge position shift and thereby the accuracy of the observed image cannot be maintained.

<Moiré Interference Pattern>

The moiré interference pattern is a phenomenon appearing between two periodic patterns being superimposed, wherein the periodicity of one periodic pattern is slightly different from that of the other periodic pattern. FIG. 1 shows an example. When an absolute value of "b" is extremely smaller than "t", there are a structure having pitch "t" and a structure having pitch "s" (=t+b, |b|<<t) being close to this pitch "t", in one-dimension. A superposition of these structures generates a new and a large pitch "m". Here, "m" satisfies with the below formulas:

$$1/m = 1/t - 1/s$$

$$m = st/(s-t) = t(t+b)/b.$$

Such a periodic pattern observed in the image is called "moiré fringe".

Sometimes, moiré fringe occurs accidentally in the case of a scanning pitch being close to a pitch length of the measured object. The scanning pitch works as the periodic pattern in this case. The embodiments show a method for scanning microscopy using the phenomena of a large moiré periodicity appearing from a small difference of pitch lengths.

<Scanning Methods and a Moiré Interference Pattern>

Scanning methods are generally classified as an analog scanning method or a digital scanning method.

The analog scanning method is a method for scanning on the scanning line continuously one by one, and its classic example is a Braun tube. There is a periodicity in a direction perpendicular to the scanning line, because it is discontinuous. Here, this pitch is indicated as "s". In the case of the pitch "s" being close to pitch "a" of the measured object, a one-dimensional moiré fringe having the pitch of "s a/(s−a)" can occur. However, in a direction of the scanning line, moiré fringe cannot occur because the scanning line is continuous. Namely, a two-dimensional moiré pattern cannot occur in the analog scanning.

Figure 2:
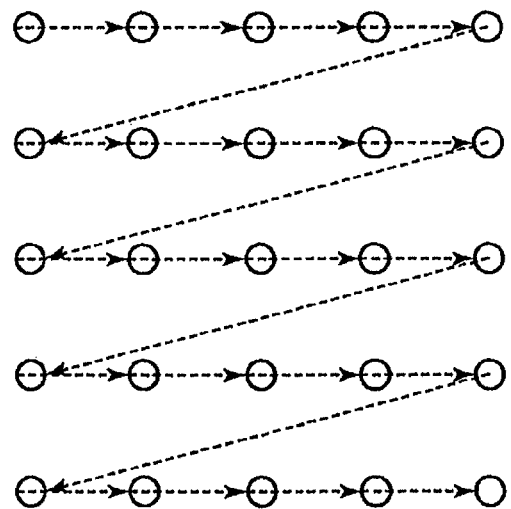
FIG. 2 explains a digital scanning method.

In the case of the digital scanning method, it scans in accordance with predetermined steps, as shown in FIG. 2. Generally, it scans sequentially on the line corresponding to a scanning line in the analog scanning, at a "1:1" constant pitch of a scanning width and a scanning step. This scanning method corresponds to a "1:1" aspect ratio and a square lattice of pixel in a digital image or a display unit.

Setting of scanning steps is mostly determined according to a resolution of a desired image, an image size, and a magnification. Generally speaking, in a middle magnification or a low magnification, a scanning step is adequately bigger than a resolution limit, and it does not cause a problem. Therefore, a scanning pitch for a necessary resolution can be set. In this case, a scanning step becomes the resolution of the image, and an area corresponding to a desired image size is scanned.

<Generation Condition of the Moiré Interference Pattern>

As shown in JP2007-315877 (kokai), an artificial lattice having an adequate periodic size on one direction compared to a resolution can make a moiré pattern by the analog scanning or the digital scanning. Here, it is noted that what seems like a two-dimensional pattern is not a two-dimensional moiré pattern, but is only superposition of the grid image.

There is a huge variety of three-dimensional crystal lattices in nature. Further, they become various two-dimensional lattices according to a direction of a cross section of the crystal lattice. So that, a useful method for obtaining a two-dimensional moiré pattern should correspond to various lattice types. In the embodiments, a moiré pattern having a desired pitch can occur by design, using a scanning microscopy which has a resolution being able to observe the crystal lattice, setting two-dimensional virtual lattice points corresponding to a periodicity of the crystal lattice, impinging a beam on each of the virtual lattice points by a stepping scan, obtaining intensity from each of the virtual lattice points, and providing the image.

<STEM and the Crystal Lattice Image>

A two-dimensional moiré pattern occurs under accidental conditions. For example, the STEM can achieve an atomic resolution by focusing the electron beam under the distance of atoms. So, the STEM can observe a two-dimensional crystal lattice image of a periodic structure of atoms. A moiré pattern may occur when an interval of crystal lattice planes on the scanning direction is close to a scanning pitch. Regarding the analog scanning, there is a possibility a moiré fringe occurs corresponding to an interval of crystal lattice planes on the scanning direction and an interval of the scanning lines. Regarding the digital scanning, there is also a possibility a moiré fringe occurs on the direction of the scanning line.

However, described in the above, known scanning methods and display methods are not enough to controllably generate two-dimensional moiré pattern from the various two-dimensional crystal structures such as a natural crystal lattice image. So, currently there are no adequate generating methods and display methods for a desired two-dimensional moiré pattern.

<Virtual Lattice Points and Step Scanning>

Next, a method for obtaining a two-dimensional moiré pattern of a crystal lattice by one embodiment is described. Although it is explained with a two-dimensional lattice space and a two-dimensional reciprocal lattice space below, it can be applied similarly with a three-dimensional lattice space and a three-dimensional reciprocal lattice space.

In a well-known digital scan, square-lattice points in series are scanned. The square-lattice points are set naturally by determining the scanning step. And pixels are displayed on 1:1.

Figure 3:
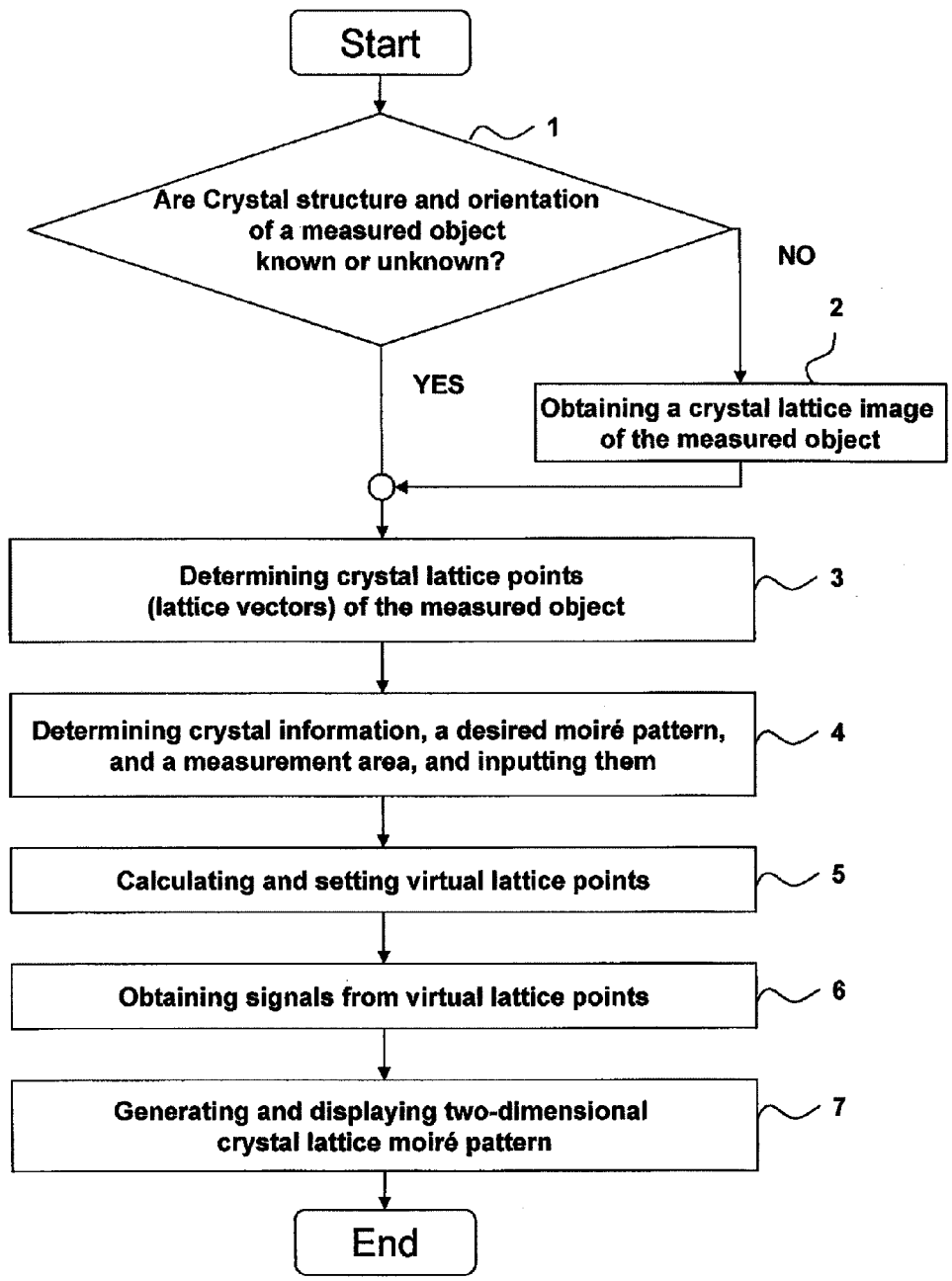
FIG. 3 is a flow chart showing a method for obtaining two-dimensional moiré pattern of a crystal lattice by one embodiment.

The method, which can be implemented by a processor based on processor executable instructions stored on a tangible computer readable medium, for obtaining a two-dimensional moiré pattern of a crystal lattice by the embodiments, can be carried out according to the procedure shown in FIG. 3.

First, the method judges whether a crystal structure, a size, and a direction of the measured object are known or unknown (block 1). In the case of unknown (NO in block 1), a crystal lattice image of the measured object is obtained (block 2). A STEM can obtain a crystal lattice image at a high resolution. Alternative methods are an electron beam diffraction method, an x-ray diffraction method, and so on. These methods can figure out the crystal structure and the orientation. If a STEM is used in this step, a crystal lattice image at a high resolution can be obtained from a perfect crystal area. Thereby, the strain distribution of a lattice can be figured out intuitively, as compared with the below-mentioned homothetic moiré pattern.

Next, lattice vectors a1, a2 are determined by an integral linear combination of the primitive vectors (block 3). The primitive vectors show the basic periodicity of the atomic arrangement of the two dimensional crystal structure in the real space. The cell vectors a1, a2 are representative of periodicities in the crystal. The cell vectors a1, a2 may be primitive unit vectors, and may also be an integral linear combination of multiple primitive unit cell vectors. For instance, cell vectors are decided to become near size corresponding to a preferable number of pixels, under the appropriate obtaining time, in the desired scale for a moiré pattern. From the points repeated by the cell vectors, two-dimensional crystal lattice points can be described. Here, crystal lattice points are representative points showing the periodic structure, so that these are not limited at the positions of atoms. Crystal lattice points can be any points in the lattice.

Figure 4:
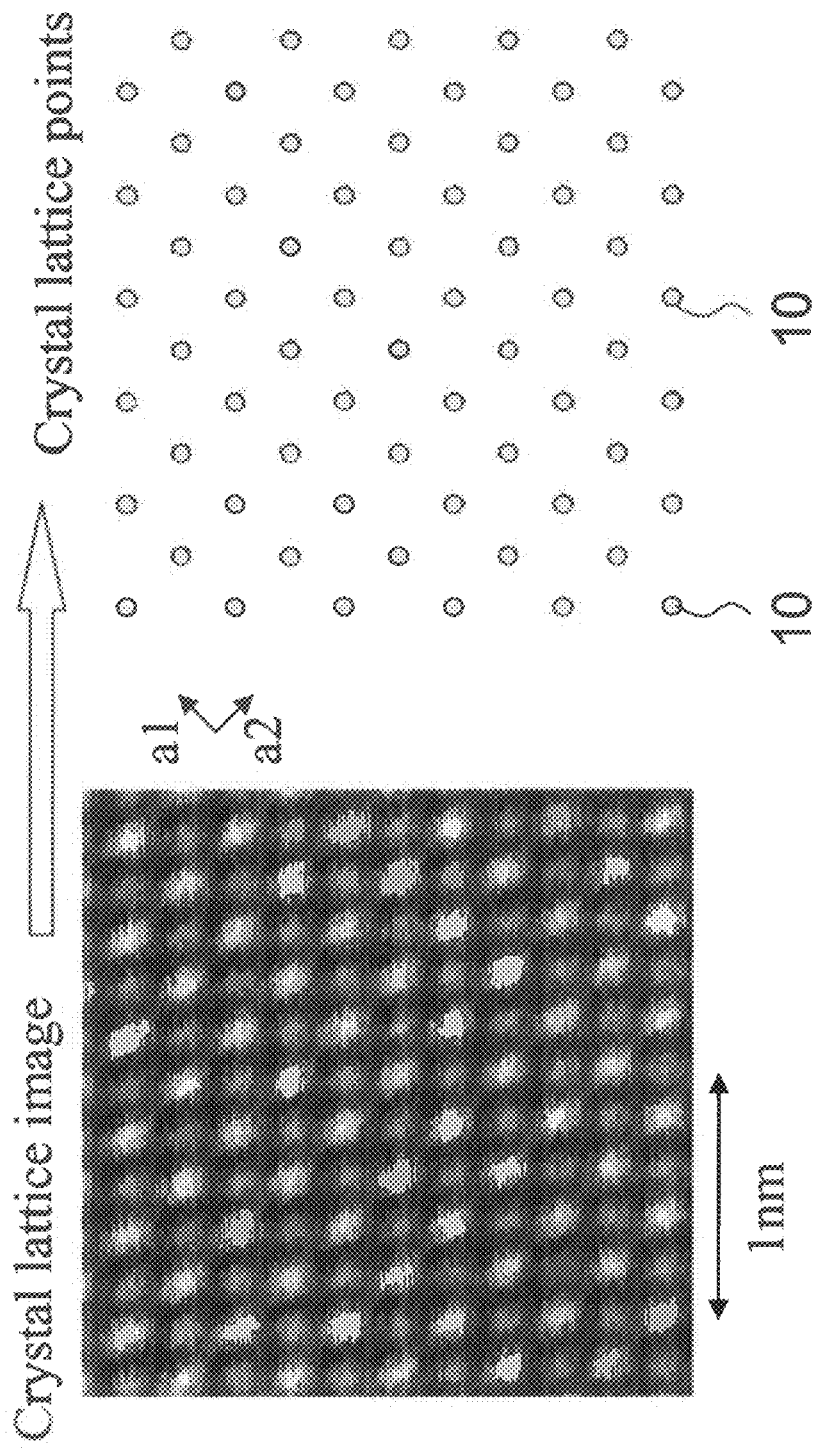
FIG. 4 shows a relationship between a crystal lattice image and crystal lattice points.

How to grasp and decide the crystal lattice points is explained by using a STEM as an example. In the case of a crystal lattice image shown in FIG. 4 obtained by a STEM, basic unit vectors are obtained from a periodic structure of a crystal lattice image, and these are determined as crystal lattice vectors a1, a2. An arbitrary point in the crystal lattice is decided as a start point. Positions which are repeated in the crystal cell vectors from the start point become crystal lattice points 10. Each crystal lattice point 10 is an equivalent within the crystal. A large enough observation area covers a few pitches being able to make perceptible the structure of crystal and the orientation. In this way, crystal information, a moiré pattern to acquired, and the observation range are determined, and these are input into the STEM control unit (block 4). Regarding blocks 3 and 4 in FIG. 3, a control unit (described later) will automatically implement the processes therein.

Fourier transform for periodic analysis is also effective, to accurately grasp the size and the orientation of primitive vectors of a crystal lattice. By two-dimensional Fourier transforming a lattice image in the real space, a periodicity of a crystal lattice image appears as points in a reciprocal lattice space (an amplitude parameter of the Fourier space). In this reciprocal lattice space, a unit of points being close to an original point corresponds to reciprocal lattice vectors. So that, the size and the orientation of primitive vectors can be grasped.

Next, based on lattice vectors a1, a2 and crystal lattice points 10, positions of two-dimensional virtual lattice points on a scanning area of a crystal structure are calculated and set up (block 5). The setting method of the virtual lattice points is mentioned later.

Next, signals from the virtual lattice point are obtained (block 6). To obtain the signals for virtual lattice points, first, an incident probe irradiates or interacts on the virtual lattice points of a measured object. Second, signals, such as transmissions, reflections, and scatterings of the incident probe from the virtual lattice points, or secondary electrons or light caused by the interaction with the incident probe, are detected. Irregularity in the order of obtaining signals for virtual lattice points is sufficient, as long as units of positions for obtaining a signal and signal intensity thereof are recorded altogether. Alternatively, the method may detect and provide an image by stepped scanning adjacent points one by one, corresponding to the well-known digital scanning method. In the case of lattices other than a square lattice and a rectangle lattice, it cannot express in extension of the well-known digital scanning method. For example, in the case of an alignment of virtual lattice points 15 shown in FIG. 5A, scanning can be executed by the method shown in FIG. 5B or FIG. 5C. The method shown in FIG. 5B can realize the scanning by a combination of virtual lattice vectors s1, s2 under the established rules. The method shown in FIG. 5C can realize the scanning of virtual lattice points 15 by scanning in the direction parallel to one virtual lattice vector s1, moving a starting point by another virtual lattice vector s2, and scanning again in the direction parallel to the virtual lattice vector s1. In these cases, if the scanning rule is recorded with signals, signal obtaining positions are calculable afterwards.

Next, a two-dimensional moiré pattern of the crystal lattice is generated and displayed, based on obtained signals from the virtual lattice points (block 7).

<Generation Principle of Moiré Pattern Based on Virtual Lattice Points>

Next, a generation principle of a moiré pattern by setting virtual lattice points and how to determine virtual lattice points are explained in detail below.

In FIG. 6, when the unit for crystal lattice vectors $a_1$, $a_2$ showing crystal lattice points 10 is determined, positions for obtained signals are set as virtual lattice points 15 showing as the unit for two-dimensional periodic vectors ($s_1$, $s_2$). Then, each reciprocal lattice vector, $a_1'$, $a_2'$, $s_1'$ and $s_2'$, is determined. Here, "r" means the value of spacial resolution, and "r'" means the value of spacial resolution in the reciprocal lattice space.

($m_1$, $m_2$) means periodicity of a two-dimensional moiré pattern generated from difference of periodicities in the real space. ($m_1'$, $m_2'$) means periodicity thereof in the reciprocal lattice space. ($m_1'$, $m_2'$) can be shown as the difference between two reciprocal lattice vectors in two-dimensional reciprocal lattice space as follows:

$$m_1'=a_1'-s_1'$$

$$m_2'=a_2'-s_2'.$$

This is an extension of the idea of the one-dimensional example explained in FIG. 1. Periodicity of a moiré pattern can be shown as the difference between inverse numbers of two periodicities, as explained in FIG. 1.

Figure 7:
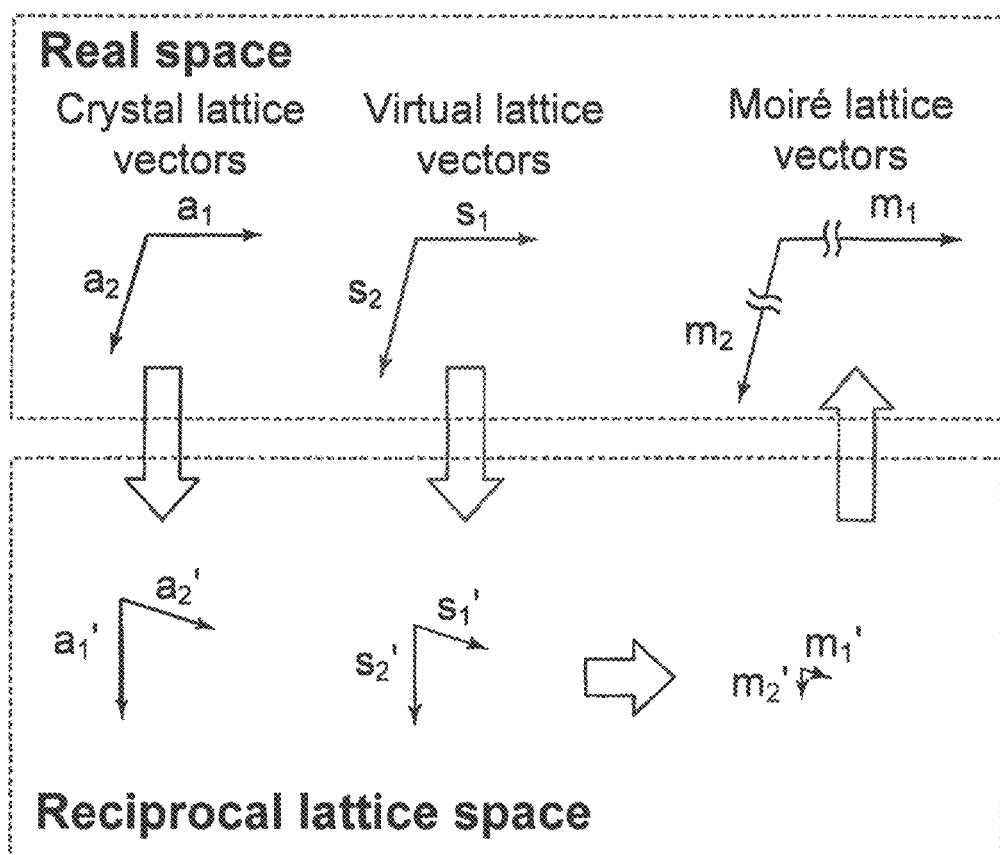
FIG. 7 explains a relationship between a real space and a reciprocal lattice space.

FIG. 7 shows these units of vectors in the real space and in the reciprocal lattice space, as an example. Units of the reciprocal lattice vectors ($a_1'$, $a_2'$) and ($s_1'$, $s_2'$) are calculated from the unit of the crystal lattice vectors ($a_1$, $a_2$) and the unit of the virtual lattice vectors ($s_1$, $s_2$). Then, a unit for periodicity of a two-dimensional moiré pattern in the reciprocal lattice space ($m_1'$, $m_2'$) is calculated from these units of reciprocal lattice vectors. A unit for periodicity of a two-dimensional moiré pattern in the real space ($m_1$, $m_2$) is determined from the unit for the periodicity of a two-dimensional moiré pattern in the reciprocal lattice space. Therefore, the virtual lattice points can be set for the virtual lattice vectors $s_1$, $s_2$ in such a way as to generate desired moiré periodic vectors $m_1$, $m_2$. And, the virtual lattice points should be set such that the unit of the virtual lattice vectors ($s_1$, $s_2$) and the unit of the crystal lattice vectors ($a_1$, $a_2$) are different from each other.

Next, the generation condition of a moiré pattern is explained.

To observe the periodicity of a two-dimensional moiré pattern in the real space ($m_1$, $m_2$), with the existence of the unit of the periodicity in the reciprocal lattice space ($m_1'$, $m_2'$), the reciprocal lattice vectors $a_1'$, $a_2'$ making up the periodicity $m_1'$, $m_2'$ in the reciprocal lattice space should exist. In other words, a periodic lattice spacing corresponding to $a_1'$, $a_2'$ can be observed. To obtain an image corresponding to a crystal structure of a moiré pattern, the minimum value in the periodic structure corresponding to lattice vectors $a_1$, $a_2$ in an image of the real space, namely a basic crystal structure, is needed to be observable. Here, "observable" means having a structure bigger than a spacial resolution "r" of the microscope. Therefore, regarding the minimum lattice vectors $a_1$, $a_2$, it is a required condition that the distance between lattice points, namely the size of the lattice vectors $a_1$, $a_2$, $|a_1|$, $|a_2|$, is bigger than the space resolution "r". The below formulas show this condition:

$$r < |a_1|;$$

$$r < |a_2|.$$

The virtual lattice vectors $s_1$, $s_2$ are the same as the above. It is a required condition that the distance between virtual lattice points, namely the size of the virtual lattice vectors $|s_1|$, $|s_2|$, is bigger than the space resolution "r". The below formulas show this condition:

$$r < |s_1|$$

$$r < |s_2|.$$

In the reciprocal lattice space, it becomes a condition that each reciprocal lattice vector showing crystal lattice spacing is smaller than a space resolution "r". This is the same as the condition which can observe the distance between lattice points in the real space. The below formulas show these conditions:

$$r' < |a_1'|$$

$$r' < |a_2'|$$

$$r' < |s_1'|$$

$$r' < |s_2'|.$$

Figure 8:
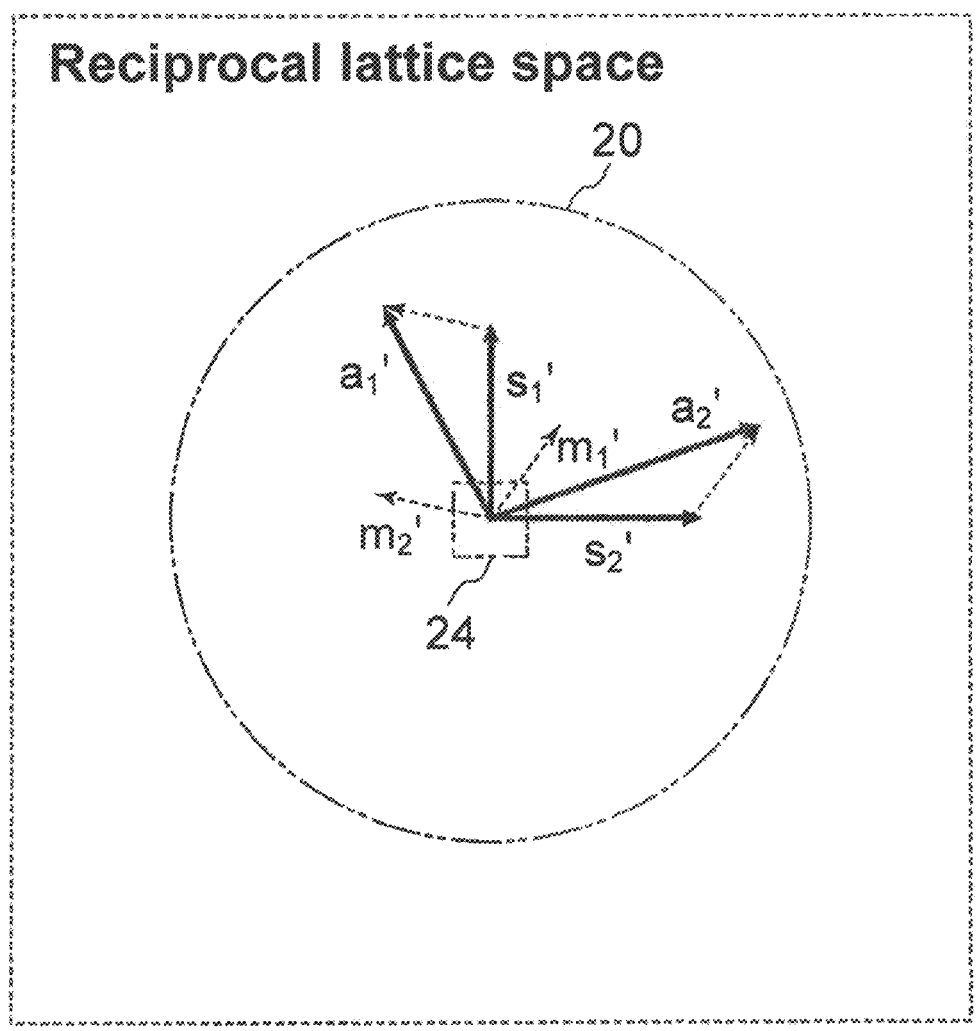
FIG. 8 explains an observable condition of a moiré pattern.

FIG. 8 shows these conditions geometrically. FIG. 8 shows a condition that these vectors $a_1'$, $a_2'$, $s_1'$, $s_2'$ exist within the circle 20 having a radius "r" in the reciprocal lattice space. When one side only of the difference vectors thereof $m_1'$, $m_2'$, namely one selected from $m_1'$ and $m_2'$, satisfies the observable condition of the moiré pattern, the moiré pattern on the one direction called the moiré fringe is observed.

Further, in the real observation, the observation area can be shown by k points on the $s_1$ direction, and l points on the $s_2$ direction (k and l are integral numbers). In the real space, the observation area is the inside area made by vectors $k \cdot s_1$ and $l \cdot s_2$. Periodicity of a moiré pattern in the real space being able to be recognized is equivalent to periodic vector $m_1$, $m_2$ being inside the above-mentioned observation area. In the reciprocal lattice space, regarding different vectors $m_1'$, $m_2'$, $s_1'$ direction factor and $s_2'$ direction factor are need to be bigger than $|s_1'|/k$, $|s_2'|/L$ respectively.

Regarding the condition of periodicity vectors $m_1$, $m_2$ being described by the plot of the virtual lattice points, $s_1$ direction factor and $s_2$ direction factor of periodicity vectors $m_1$, $m_2$ need to be bigger than the size of the virtual lattice vectors $s_1$, $s_2$, that is $|s_1|$, $|s_2|$, respectively.

The virtual lattice vectors $s_1$, $s_2$ are determined, and in consideration with the above condition, periodicity vectors $m_1$, $m_2$ being able to observe a desired direction of a moiré-pattern, and a desired periodic size thereof (FIG. 3, block 3). Next, the virtual lattice points are generated such that repeated points of the virtual lattice vectors $s_1$, $s_2$ cover the observation area (FIG. 3, blocks 4, 5). The data of the moiré pattern can be generated by obtaining signals on every point (FIG. 3, block 6).

<The Various Types of the Virtual Lattice>

Two-dimensional periodic lattices are classified into five kinds of Bravais lattices, that is, a square lattice, a rectangular lattice, a face-centered lattice, a hexagonal lattice, an orthorhombic lattice. The virtual lattice points can be classified the same as the crystal lattice. Therefore, it is possible to understand the generation of a two-dimensional moiré pattern, in the same way as the superposition of two crystals. The virtual lattice points of the embodiments can be considered as lattice points not having an inside structure in the Bravais lattice. Regarding a square lattice, signals obtained on the virtual lattice points can be shown in a "1:1" aspect ratio. In the case of the lattices other than a square lattice, when an adjoining point is displayed in order, an image cannot be expressed as-is in such a way as to have one-to-one corresponding to the position of obtaining the image. For an example, in the case of the rectangular lattice, the image will have a distorted aspect ratio. Further, in the case of the other lattices, the orientation is also distorted.

<Display of the Two-Dimensional Moiré Pattern Homothetic to the Crystal Lattice Image>

Display of the signals obtained from the virtual lattice points is explained. The strain distribution of a two-dimensional lattice on each position can be measured. It can be measured by imaging from the moiré pattern data obtained from the virtual lattice points to make it intelligible visually, and analyzing on the image. It can be also measured by calculating the obtained data directly.

Figure 9A:
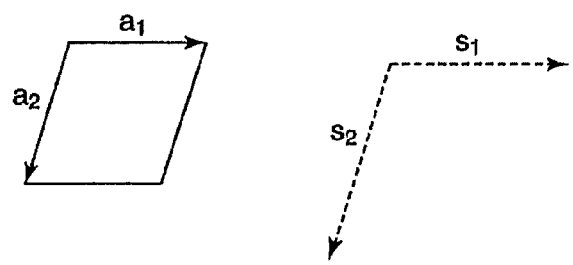
FIGS. 9A and 9B explain how to obtain detected signals when crystal lattice vectors are homothetic to virtual lattice vectors.
Figure 9B:
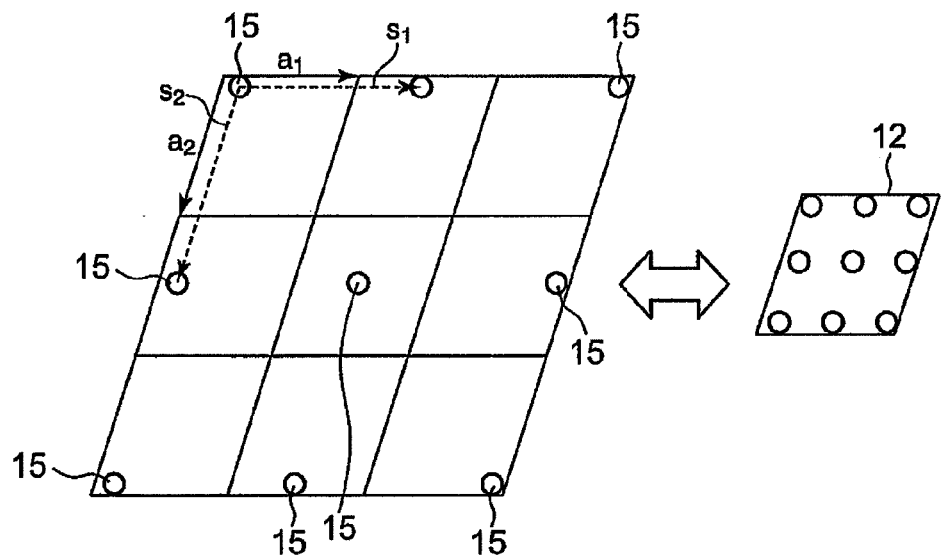

In the case of imaging, the moiré pattern changes in the combination of the virtual lattice and the crystal lattice. It is the most intelligible visually to see the moiré pattern homothetic to the high-resolution image. FIG. 9A shows the case in which the crystal lattice vectors are homothetic to the virtual lattice vectors. FIG. 9B shows the detected signals obtained from every virtual lattice point 15 that are obtained from the same points as the points within the unit cell of the crystal lattice 12 along with the vectors of crystal lattice 12. Therefore, exactly the same pattern as the crystal lattice image can be obtained by imaging. Here, it is preferable to set about 5 pixels for one periodicity, to be able to practically recognize the moiré pattern the same as the crystal lattice image. The next formula shows this preferable condition $$|s_n| < 5 \times |m_j| \ (n=1,2, j=1,2).$$

Figure 10A:
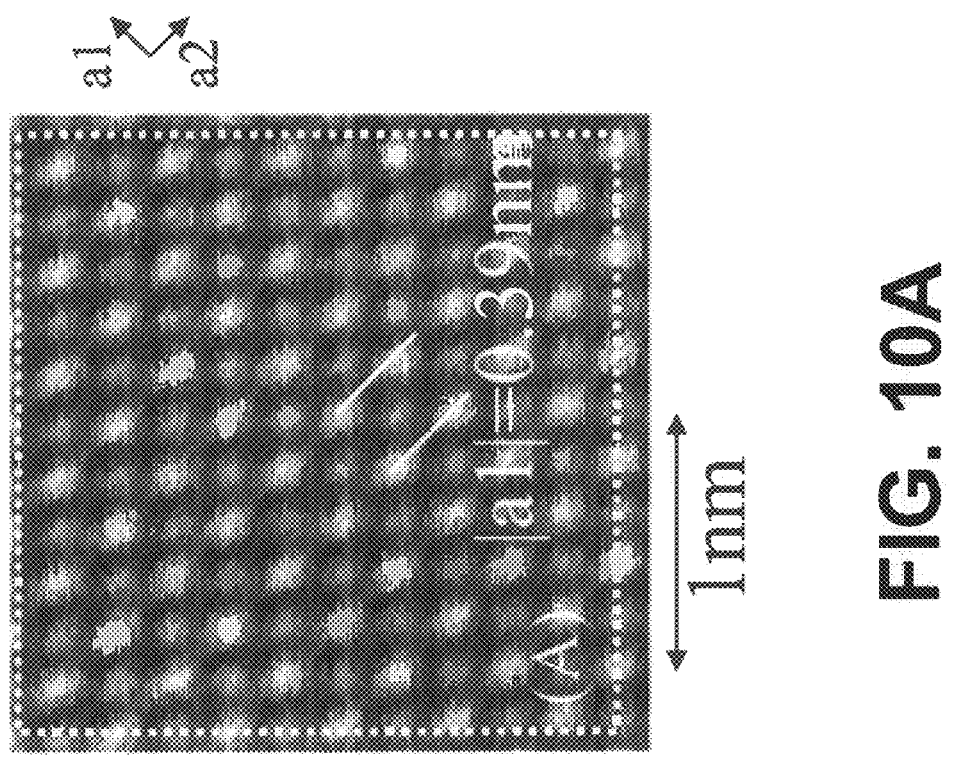
Figure 10B:
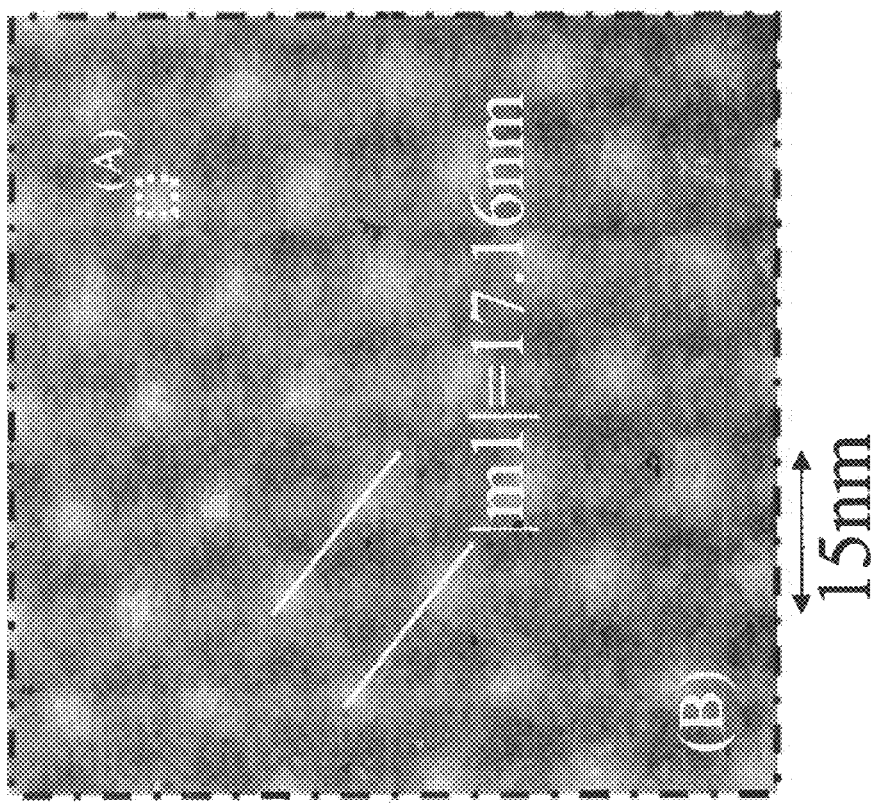

FIG. 10B shows a homothetic moiré pattern obtained from the crystal lattice image of the square lattice shown in FIG. 10A, using the STEM by the obtaining method of one embodiment. FIG. 10C shows the moiré pattern of a perfect crystal area 40 and a strained area. The crystal lattice image of the square lattice shown in FIG. 10A is obtained from the (A) area in the perfect crystal area 40 shown in FIG. 10C. The moiré pattern shown in FIG. 10B is obtained from the (B) area in the perfect crystal area 40 shown in FIG. 10C.

The crystal lattice shown in FIG. 10A is a square lattice having $a_1$, $a_2$ shown in the next formulas:

$$|a_1|=0.39 \text{ nm}$$

$$|a_2|=0.39 \text{ nm}.$$

Regarding the virtual lattice, virtual lattice points are set in such a way as to satisfy the below formulas. That is, virtual lattice vectors are homothetic to crystal lattice vectors:

$$s_1=1.023a_1, |s_1|=0.40 \text{ nm}$$

$$s_2=1.023a_2, |s_2|=0.40 \text{ nm}.$$

FIG. 10A is a moiré pattern image from the above conditions. FIG. 10B shows a homothetic image to the crystal lattice image in a large area. The scale of the homothetic image is about 44 times of the crystal lattice, and it is almost the same as the calculated value m1=44.5×a1. Scanning time is about square of the scale, although it depends on the observation conditions. In this case, the image corresponding to a crystal lattice can be obtained in a time of about 1/2000, as compared with a high-resolution image having a same area.

<Real Example of Strain Observation>

It is intelligible visually to see disorder from the perfect crystal on the periodic direction of virtual lattice points by the above obtaining method. It is also easy to calculate the strain amount of the lattice as the mentioned below. There is a perfect crystal in the area 40, corresponding to the upper right of the crystal inside in FIG. 10C. On the other hand, the edge in FIG. 10C shows the curved lattice described in the moiré pattern, reflecting the slightly out of the atom alignment by the strain.

<Analysis of a Strain Area>

If a crystal lattice vector in the strain area is "$a_{dn}$" (n=1,2), a reciprocal lattice vector is "$a_{dn}'$" (n=1,2), and a lattice vector of a moiré pattern obtained in the strain area is "$m_{dn}$", and a reciprocal lattice vector of a moiré pattern obtained in the same is "$m_{dn}'$", the relationship between them is the below:

$$m_{dn}'=s_n'-a_{dn}'.$$

A difference of the reciprocal lattice vector of a moiré pattern in the strained area and the perfect crystal area is equal to a difference of the crystal lattice vector in the strained area and the perfect crystal area, namely $$m_{dn}'-m_n'=-(a_{dn}'-a_n').$$

Figure 11:
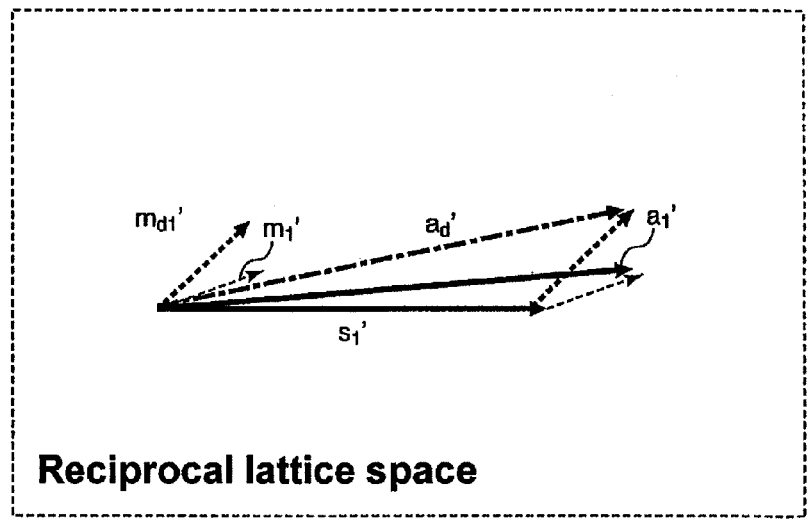
FIG. 11 explains moiré reciprocal lattice vectors in a normal area and a strain area.

Here, "$a_n'$" (n=1,2) expresses a crystal reciprocal lattice vector in a normal area (the perfect crystal area), and "$m_a'$" (n=1,2) expresses a moiré reciprocal lattice vector in a normal area. From this relationship, shown in FIG. 11, a crystal reciprocal lattice vector in a strain area is obtained and a lattice size in the strain area in the real space becomes calculable.

Figure 12:
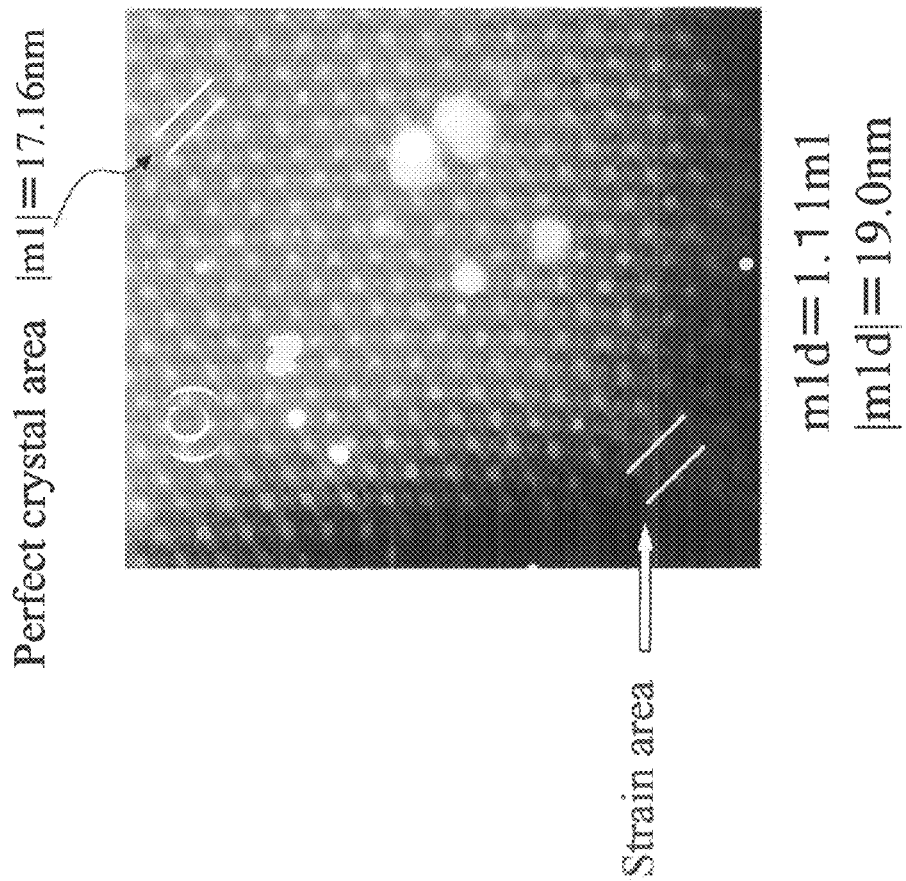
FIG. 12 explains how to calculate a strain from a moiré pattern.

As shown in FIG. 12, a strain of the crystal lattice image on the moiré pattern is analyzable by the above-mentioned method. Misalignment of a moiré pattern is 11% on the $m_1$ direction at the left lower in the crystal edge of FIG. 12. In this case, m1=44×$a_1$, and $m_{d1}$=1.11×$m_1$=44×1.11×$a_1$. From these calculations, $a_{d1}$=1.002$a_1$. That shows the strain area has the 0.2% strain on the $a_1$ direction compared to the perfect area within the crystal (perfect crystal area). In this manner, from misalignment of a two-dimensional moiré pattern (corresponding to about 2 nm) in the large scale such as 44 times of the crystal lattice, a slight strain (corresponding to 0.00078 nm) such as 0.2% of the crystal lattice which is 1 nm or smaller can be calculated.

<How to Display in 1:1 Aspect Ratio Using the Signals from the Virtual Lattice Points>

Next, how to display the signals, in the case of obtaining signals by setting virtual lattice points, is explained. As mentioned above, a usual image display is on condition of raster scanning of an aspect ratio 1:1. The raster scanning of 1:1 corresponds to selecting the square lattice as virtual lattice points in this embodiment. Namely, it is the case that virtual lattice vectors $s_1$, $s_2$ have a same size and are both made at a 90 degree angle, and the detected signals are displayed on the pixels having a homothetic shape to virtual vectors $s_1$, $s_2$. Therefore, one method is that a display unit is considered as one having lattice points, and the detected signals are arranged corresponding to the lattice points of the display unit and displayed.

When it is displayed as a usual image having a "1:1" aspect ratio, a rectangular lattice can change the aspect ratio. Regarding the other lattices of a face-centered lattice, a hexagonal lattice, and an orthorhombic lattice, not only an aspect ratio but also an angle is distorted compared to the square lattice. Therefore, in the case of the orthorhombic lattice 50 shown in FIG. 13 A, one signal can be drawn by multiple pixels, to display on the pixels having 1:1 the square lattice points from the signals obtained at the position of the virtual lattice points. Namely, as shown in FIGS. 13A, 13B, the signal is drawn by smaller pixels than virtual lattice points. That corresponds to a simple-expansion display. However, in reality, the number of pixels in the display unit is limited. Therefore, as shown in FIG. 13C, it is able to be displayed using a well-known contracting method such as bi-cubic method, without spoiling the relationship between position of obtained data and its intensity. That is, the two-dimensional moiré pattern of the crystal lattice is displayed by scaling or rotating, corresponding to the aspect ratio of the display unit.

<Display and Analysis for Square Virtual Lattice Points>

When the square virtual lattice points are set to the crystal lattice other than the square lattice, a pattern having crossed moiré fringe can be generated, although a homothetic pattern to the crystal lattice cannot be obtained. A conventional digital beam controller of a STEM can perform a square periodic scan and a rectangle periodic scan, so that an existing microscope can be used. A moiré pattern data in this case has a distorted shape in the XY ratio and in an angle visually. As shown in the FIG. 11, same as the mentioned strain analysis, misalignment of two-dimensional periodicity can be detected by calculating the difference with a perfect periodic crystal, in accordance with the relationship with lattice vectors of virtual lattice points.

Explained in the above, this embodiment uses a scanning microscope able to observe the crystal lattice in the real space, calculates and sets virtual lattice points to generate an arbitrary two-dimensional moiré pattern corresponding to the periodicity of the crystal lattice, scans these virtual lattice points step by step, and detects the signals. Regarding the lattice other than the square lattice, a normal dot image cannot be obtained. Thus, coequal information to a high-resolution image of the crystal lattice can be obtained, by making a one to one image from the data obtained by a rectangle or an orthorhombic periodical scan, or by inverse analyzing the moiré pattern without imaging.

The embodiment can generate the two-dimensional moiré interference pattern of a crystal lattice image in a short scan time being equal to scanning of a small area. This two-dimensional moiré pattern is homothetic to a crystal lattice image and equals a crystal lattice pattern directly measured at high resolution (for example, ten million times magnification). And the two-dimensional moiré pattern is obtained by scanning a large area at middle or low magnification (e.g., 500 thousands times magnification).

Furthermore, the embodiment can realize several methods using two-dimensional periodicity of the crystal lattice in a large area without increasing an obtaining time. The embodiment can display an image zooming up the crystal periodicity in a measurement area at a low magnification. Thus, the distribution of the two-dimensional lattice strain and so on can be interpreted intuitively and can be analyzed quantitatively.

The embodiment also prevents a sample from damage and contamination caused by a convergent beam to a tiny area by obtaining an image with high-resolution. It also has an effect to control the beam condition at the low magnification.

<Microscope Executing the Above Mentioned Method>

Next, a scanning microscope executing the method of obtaining the two-dimensional moiré pattern of a crystal lattice by the embodiment is explained.

Figure 14:
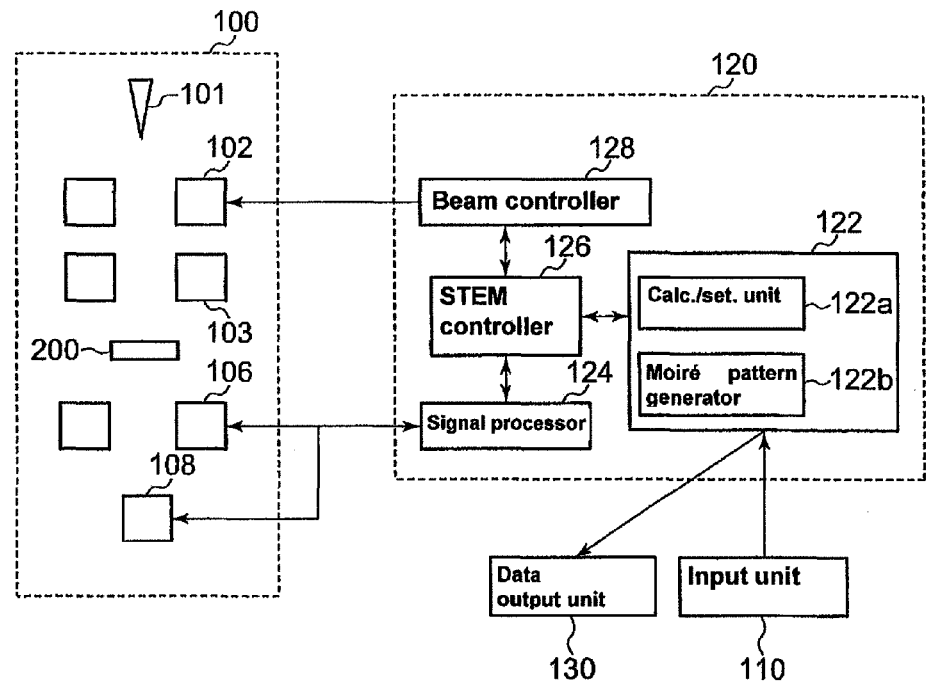
FIG. 14 shows an apparatus executing a method for obtaining a two-dimensional crystal lattice moiré pattern by one embodiment.

Hereinafter, a STEM is used as an example of an apparatus scanning virtual lattice points, as shown in FIG. 14. STEM main unit 100 includes a beam generator 101 generating charged particles including electrons. A charged-particle beam emitted from beam generator 101 is deflected by an electromagnetic field generated from a beam deflection section 102, and is converged on the desired position of a thin-film sample (crystal structure) 200, through objective lens 103. Signals generated from the sample 200 are detected by an ADF (annular dark field) detector 106 and a BF (bright field) detector 108. The electromagnetic field for deflection is controlled by a current or voltage sent from control unit 120.

The apparatus includes an input unit 110 inputting parameters for setting the virtual lattice points (for example, the data at S3, S4 shown in FIG. 3), a control unit 120, and a data output unit 130, to set the virtual lattice points and detect the signals from the virtual lattice points in the embodiment. Control unit 120 includes a CPU (central processing unit) 122, signal processor 124, STEM controller 126, and beam controller 128.

Signal processor 124 operates as an analog-digital converter for example, That is, signal processor 124 converts the detected signals (current signals for example) detected by ADF detector 106 or BF detector 108 into digital signals and supplies them to the control unit 120.

CPU 122 calculates and sets the positions of virtual lattice points on a scan plane of the sample (crystal structure) by calculation/setting unit 122a, based on the input data from input unit 110. CPU 122 generates a two-dimensional moiré pattern of the crystal structure by moiré pattern generation unit 122b, based on the detected signals obtained via signal processor 124 and STEM controller 126. This generated two-dimensional moiré pattern of the crystal structure is displayed as an image on data output unit 130.

Inputting of the parameters for setting virtual lattice points may input coordinates of virtual lattice points, or may make calculation/setting unit 122a in CPU 122 calculate the positions of virtual lattice points, by inputting virtual lattice vectors on an obtained area. Inputting of the coordinates of virtual lattice points and virtual lattice vectors may input using absolute coordinates used in control unit 120, using relative coordinates based on the crystal lattice in sample 200, or using relative vectors based on the crystal lattice vectors in sample 200. In the second and the third case, CPU 122 stores information of crystal lattice vectors that it can convert into absolute coordinates. Here, information of the crystal lattice is obtained previously from the image thereof using the STEM main unit 100, or it is obtained previously by inputting the crystal lattice information.

Calculation/setting unit 122a in CPU 122 sets the positions of virtual lattice points. STEM controller 126 sends control signals for beam position to beam control unit 128 such that the beam is emitted on the positions of virtual lattice points. STEM control unit 126 obtains the detected signals in synchronization via the signal processor 124, and sends the obtained detected signals to CPU 122. A two-dimensional moiré pattern of the crystal lattice is generated based on these detected signals, by moiré pattern generator 122b.

Figure 15:
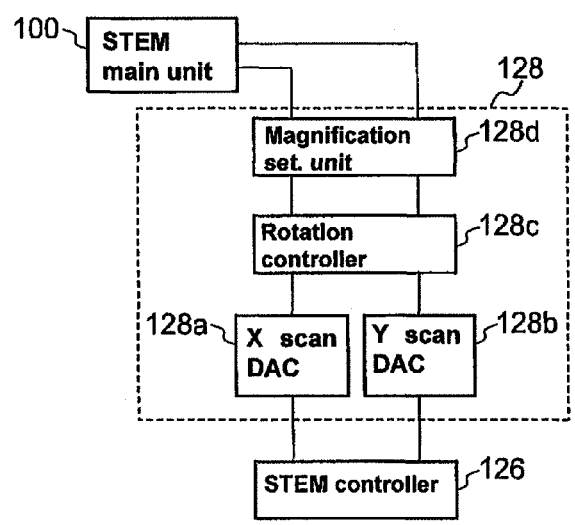
FIG. 15 is a block diagram of a beam controller.

Beam controller 128 sends the control signals to beam deflection section 102, based on the control signals for beam position from STEM controller 126, and controls the beam position by controlling the electromagnetic field generated from beam deflection section 102. For example, when beam deflection section 102 includes two sets of coil pairs and these coils generate a magnetic field controlling X, Y directions of the beam, beam controller 128 converts the control signals into current signal pairs corresponding to the X,Y directions. FIG. 15 shows one example of beam controller 128. Beam controller 128 includes an X scan DAC (digital-analog converter) 128a, Y scan DAC 128b, rotation controller 128c, and magnification setting unit 128d.

Applicants recognize it is better to control deflection in a smaller position than the distance between atom lattices, to maintain the electrical beam correctly at the position of desired virtual lattice points. As shown in FIG. 15, the beam position of the STEM is controlled by the X scan DAC 128a, Y scan DAC 128b, rotation controller 128c, and magnification setting unit 128d, in beam controller 128. In the case of DAC 128a and 128b having 12 bits, it becomes 4096 ($=2^{12}$) gradation. Regarding the control of the beam position to be smaller than the resolution of atom lattices, for example, the magnification is set in magnification setting unit 128d, such that the minimum step (step size) is 0.01 nm. Then, the measurement range becomes 0.01 nm×4096=40.96 nm as the maximum amplitude. To measure a larger area at low magnification, the magnification at magnification setting unit 128d changes and makes the measurement range larger. However, to increase a magnification means to increase minimum pitch. For example, because 1 nm becomes the minimum pitch in the image having 100-times as large an area, it is impossible to realize detailed control of the beam under the atomic level, 0.1 nm and below. In the embodiment, it may be better to use DAC having more detailed output gradation, because the embodiment needs to scan a large area and to control the beam by 0.1 nm or below.

As a modification, beam controller 128 may include a transforming section in addition to or instead of rotation controller 128c and magnification setting unit 128d. $I_x$ and $I_y$ are pairs of control signals, for steps on the X direction and on the Y direction, outputting from DAC 128a and 128b, respectively. The transforming section converts signal steps for corresponding to virtual lattice points such as by the below formulas:

$$I_x'=cI_x+dI_y$$

$$I_y'=eI_x+fI_y.$$

Here, "c", "d", "e", and "f" are conversion coefficients. Usually, X scan and Y scan has the same magnification and the same rotation. On the other hand, in the modification, X scan and Y scan has each magnification and each rotation independently and respectively, by the transforming section.

While certain embodiments have been described, these embodiments have been presented by way of example only, and are not intended to limit the scope of the inventions. Indeed, the novel methods and apparatuses described herein may be embodied in a variety of other forms; furthermore, various omissions, substitutions, and changes in the form of the methods and apparatuses described herein may be made without departing from the spirit of the inventions. The accompanying claims and their equivalents are intended to cover such forms or modifications as would fall within the scope and spirit of the inventions.

The invention claimed is:

1. A method of generating a desired crystal lattice moiré pattern of a crystal structure of a measured object, the method comprising:
   determining crystal lattice points of the measured object;
   calculating a plurality of virtual lattice points arranged periodically on a scanning plane of the crystal structure in accordance with the crystal structure, an orientation of the crystal structure, and information about the desired crystal lattice moiré pattern; and
   detecting signals from the plurality of virtual lattice points using a Scanning Transmission Electron Microscope (STEM); and
   generating the desired crystal lattice moiré pattern based on the detected signals.

2. The method according to claim 1, wherein a distance between adjoining virtual lattice points is larger than a resolution of the STEM.

3. The method according to claim 1, wherein virtual lattice vectors corresponding to the virtual lattice points are set up to be homothetic to crystal lattice vectors on the scanning plane of the crystal structure.

4. The method according to claim 1, further comprising:
   subjecting the crystal lattice moiré pattern to scaling or rotating corresponding to an aspect ratio of pixels in a display unit; and
   displaying the crystal lattice moiré pattern by the display unit.

5. The method according to claim 1, further comprising calculating a strain amount of the crystal lattice points, based on the detected signals.

6. The method according to claim 1, wherein the detecting signals includes synchronized detecting of plural signals at each of the plurality of virtual lattice points.

7. The method according to claim 1, wherein the plurality of virtual lattice points are in a square lattice.

8. The method according to claim 4, wherein the plurality of virtual lattice points are in a rectangular lattice.

9. The method according to claim 4, wherein the plurality of virtual lattice points are in a face-centered lattice, a hexagonal lattice, or an orthorhombic lattice.

10. The method according to claim 4, wherein the plurality of virtual lattice points are in one lattice selected from a face-centered lattice, a hexagonal lattice, or an orthorhombic lattice, and one of the detected signals is drawn by multiple pixels in the display unit.

11. A method of obtaining a controllably generated moiré pattern of a crystal structure of a measured object, the method comprising:
    determining crystal lattice points of the measured object;
    setting a predetermined desired moiré pattern which has a desirable size and orientation;
    calculating a plurality of virtual lattice points arranged periodically on a scanning plane of a whole measurement area in accordance with the determined crystal structure, an orientation of the crystal structure, and information about the desired moiré pattern;
    detecting signals from the virtual lattice points using a Scanning Transmission Electron Microscope (STEM); and
    recording the signal intensity corresponding to the virtual lattice points as the moiré pattern.

12. A system which generates a desired crystal lattice moiré pattern of a crystal structure of a measured object, the system comprising:
    a receiver configured to receive information about the desired crystal lattice moiré pattern;
    a calculator programmed to:
    i) determine crystal lattice points of the measured object;
    ii) calculate a plurality of virtual lattice points arranged periodically on a scanning plane of the crystal structure in accordance with the crystal structure, an orientation of the crystal structure, and the information about the desired crystal lattice moiré pattern;
    a Scanning Transmission Electron Microscope (STEM) configured to detect signals from the virtual lattice points; and
    a generator configured to generate the desired crystal lattice moiré pattern based on the detected signals.

* * * * *